(12) United States Patent
Fadel

(10) Patent No.: US 10,765,310 B2
(45) Date of Patent: Sep. 8, 2020

(54) LARYNGOSCOPE WITH BLADE POSITION ADJUSTMENT

(71) Applicant: Dina Abi Fadel, New York, NY (US)

(72) Inventor: Dina Abi Fadel, New York, NY (US)

( * ) Notice: Subject to any disclaimer, the term of this patent is extended or adjusted under 35 U.S.C. 154(b) by 429 days.

(21) Appl. No.: 15/044,112

(22) Filed: Feb. 16, 2016

(65) Prior Publication Data
US 2017/0035284 A1 Feb. 9, 2017

Related U.S. Application Data

(60) Provisional application No. 62/200,383, filed on Aug. 3, 2015.

(51) Int. Cl.
*A61B 17/24* (2006.01)
*A61B 1/267* (2006.01)
*A61B 1/00* (2006.01)

(52) U.S. Cl.
CPC .......... *A61B 1/267* (2013.01); *A61B 1/00071* (2013.01)

(58) Field of Classification Search
CPC .................................................... A61B 1/267
USPC ....... 600/185–200, 214, 215, 216, 219, 220, 600/222, 224, 225
See application file for complete search history.

(56) References Cited

U.S. PATENT DOCUMENTS

| | | | | |
|---|---|---|---|---|
| 4,815,451 A * | 3/1989 | Bauman | ................ | A61B 1/267 600/198 |
| 5,584,795 A * | 12/1996 | Valenti | .................. | A61B 1/042 600/196 |
| 5,722,935 A * | 3/1998 | Christian | ........... | A61B 17/0281 600/204 |
| 2003/0181789 A1* | 9/2003 | Mazzei | ................ | A61B 1/267 600/188 |
| 2006/0247496 A1* | 11/2006 | Tjong Joe Wai | ...... | A61B 1/267 600/184 |
| 2007/0060794 A1* | 3/2007 | Efinger | ................. | A61B 1/267 600/219 |
| 2008/0108877 A1* | 5/2008 | Bayat | ..................... | A61B 17/02 600/214 |
| 2008/0146879 A1* | 6/2008 | Pacey | ..................... | A61B 1/05 600/188 |
| 2009/0247833 A1* | 10/2009 | Tanaka | ................ | G09B 23/285 600/188 |
| 2014/0179998 A1* | 6/2014 | Pacey | ................... | A61B 17/02 600/103 |

* cited by examiner

*Primary Examiner* — Amy R Sipp
(74) *Attorney, Agent, or Firm* — Kali Law Group, P.C.

(57) ABSTRACT

A laryngoscope having a blade with various motion functions. The motion functions can be invoked by pushbutton type controls on the handle of the laryngoscope, and can be accomplished mechanically, electrically, or in combination. In addition to one motion suitable for lifting the tongue, the blade can also be adjusted as to its direction of projection from the handle and distance from the handle.

60 Claims, 4 Drawing Sheets

LARYNGOSCOPE WITH BLADE POSITION ADJUSTMENT

CROSS-REFERENCE TO RELATED APPLICATIONS

This application claims the benefit of priority from U.S. Provisional Patent Application Ser. No. 62/200,383 (filed Aug. 3, 2015). The entire content of Provisional Patent Application Ser. No. 62/200,383 is incorporated herein by reference in its entirety.

FIELD OF THE INVENTION

The present invention relates to laryngoscopes, and more particularly, to a laryngoscope having a blade repositionable relative to the handle.

BACKGROUND OF THE INVENTION

Laryngoscopes are used to reposition body organs such as the tongue, for example, to prepare for intubation during medical procedures. A laryngoscope is grasped by and manually manipulated to achieve desired reposition of the body organs. However, a considerable force may be necessary to achieve the desired repositioning. Application of such force may risk injury to both the patient and, also potentially, the operator. Appropriate positioning of the laryngoscope is critical for successful intubation.

SUMMARY OF THE INVENTION

The present invention addresses the above stated situation by providing a laryngoscope which has mechanism to facilitate lifting and other movements of the blade for optimal visualization of the larynx for securing the patient airway while avoiding excessive maneuvering and force. The novel laryngoscope enables force applied to the blade of the laryngoscope to be great enough to accomplish desired manipulation, yet limited so as not to result in injury to the patient and bodily strain to the operator of the laryngoscope.

To this end, in a powered realization of the disclosure, the novel laryngoscope has electrically powered motion functions of the blade, which motion functions can be invoked by pushbutton type controls on the handle of the laryngoscope. In addition to one motion suitable for lifting the tongue, the blade can also be adjusted as to its direction of projection from the handle. This may relieve a user from having to release the handle of the laryngoscope from tight grasp. If releasing the handle, the user may be obliged to restart a tongue moving procedure.

Available movements of the blade may be accomplished mechanically. In one realization of the disclosure, a sliding movement of the blade relative to the handle relieves pressure of the operator's effort.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
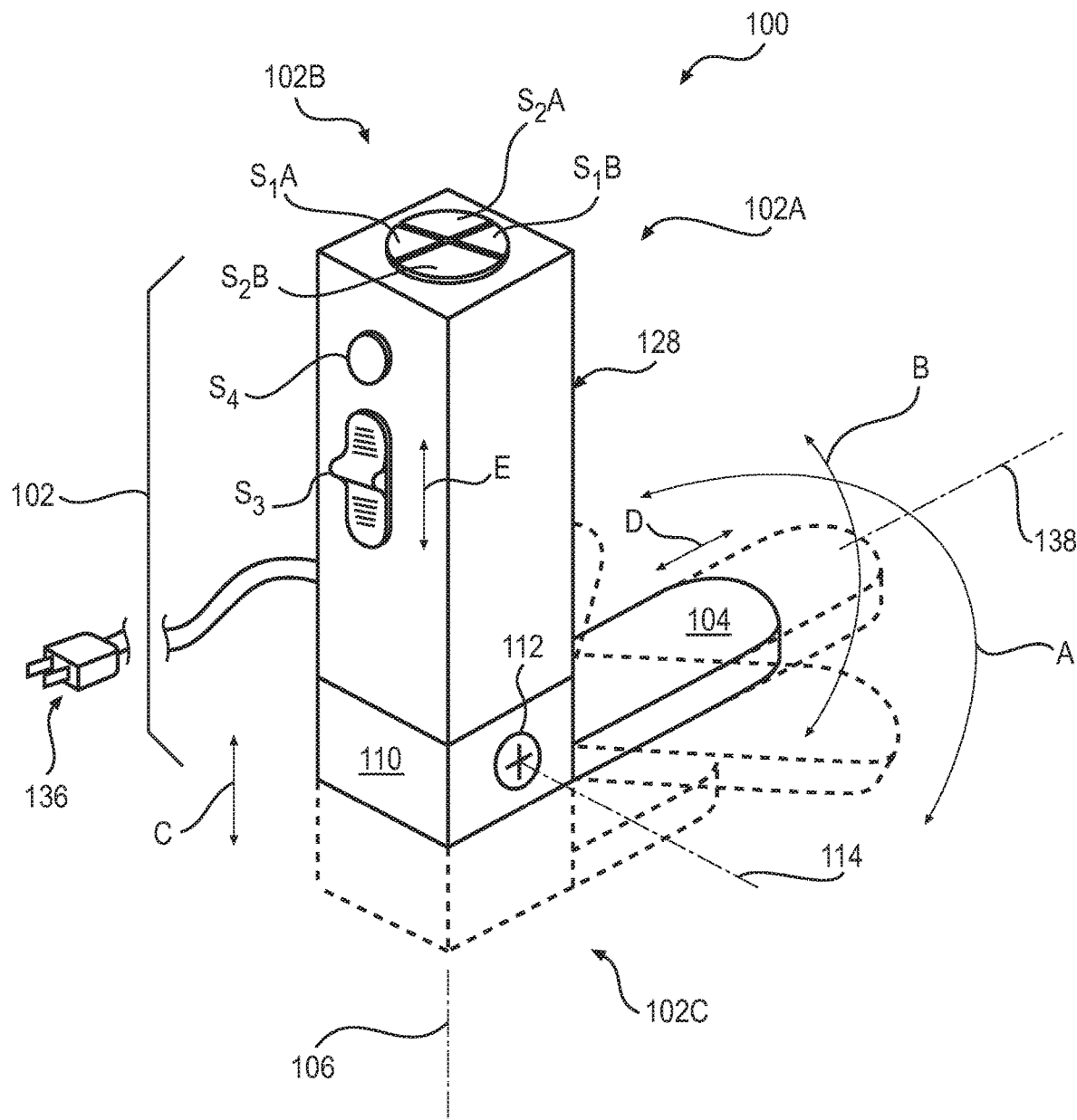
FIG. 1 is a diagrammatic perspective view of a laryngoscope, according to at least one aspect of the disclosure.

Referring first to FIG. 1, according to at least one aspect of the disclosure, there is shown a laryngoscope 100 comprising a handle 102 having a front side 102A, a proximal end 102B, and a distal end 102C, a blade 104 movably coupled to handle 102 and projecting from the front side 102A and proximate distal end 102C of handle 102, and a mechanism, such as one or more motors and one or more gears, for moving blade 104 relative to handle 102. The front side 102A may comprise, for example, a flat surface thereby providing a front side to handle 102, a rounded surface thereby providing a front face to handle 102, a dimple surface, a ridged surface or any suitable grip surface made up of, for example, ridges to provide a grip surface; in short, front side 102A is not limited to a particular overall shape or appearance. Blade 104 is that portion of laryngoscope 100 which contacts and lifts the tongue or other body tissue (none shown) being manipulated by medical personnel. Handle 102 has length along axis 102D. In FIG. 1, four positional adjustments are represented. Representative alternative positions of blade 104 relative to handle 102 are indicated in broken lines throughout FIGS. 1-5.

For semantic convenience in explaining these positional adjustments, laryngoscope 100 is shown in what will be called an upright position of use. It should be noted at this point that orientational terms such as upright, right, and left, etc., refer to the subject drawing as viewed by an observer. The subject matter could obviously change depending on orientation of the user's hand. Therefore, orientational terms must be understood to provide semantic basis for purposes of description only, and do not imply that their subject matter can be used only in one position.

The mechanism for moving blade 104 relative to handle 102 may comprise, for example, at least one electric motor, and a linkage arranged to move or guide blade 104 responsive to operation of the at least one motor.

The present invention is not limited to a specific type of laryngoscope. For example, the laryngoscope 100 can comprise a non-flexible or flexible handle 102.

Figure 2:
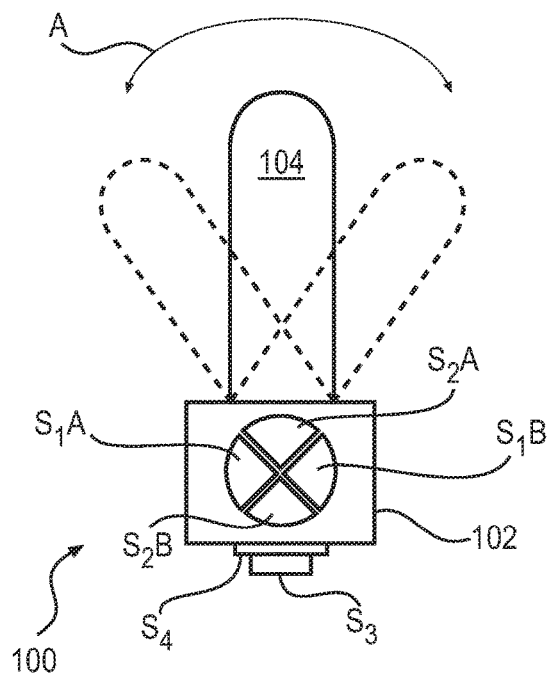
FIG. 2 is a diagrammatic top plan view of the laryngoscope of FIG. 1, according to at least one aspect of the disclosure.
Figure 6:
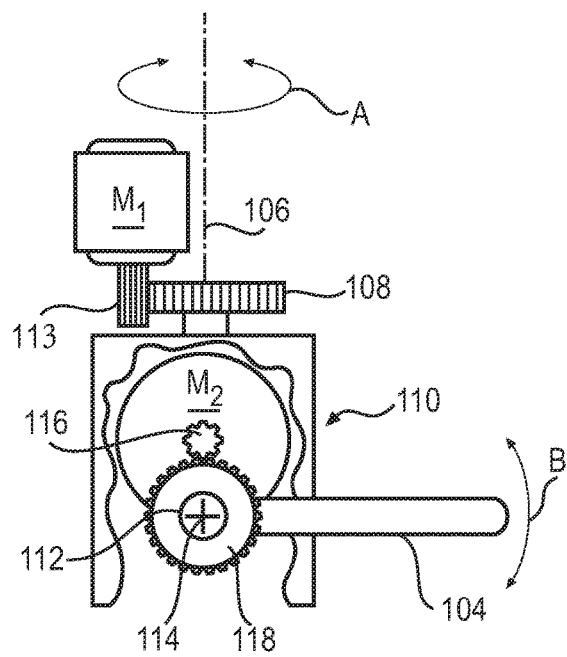
FIG. 6 is a diagrammatic side detail view of internal components of the laryngoscope of FIG. 1, according to at least one aspect of the disclosure.

Referring also to FIG. 2, blade 104 is pivotally movable to the right and to the left (this right-and-left motion is indicated by arrow A) with respect to axis 106 extending along the length of handle 102 (FIG. 6). Blade 104 is moved as desired along the path indicated by arrow A. This movement is initiated by pushbutton switch S1. Switch S1 comprises two pushbutton switches S1A and S1B. Switches S1A and S1B are arranged to alternate polarities of DC current applied to motor M1 (see FIG. 6) as well as making and breaking circuitry (see FIG. 9) serving motor M1, the latter reversibly effecting movement of blade 104 along the path indicated by arrow A, as will be further explained hereinafter.

Blade 104 may be configured in ways other than as depicted in the drawing figures. For example, blade 104 may be curved, straight, or may be configured to cooperate with the anatomy.

Handle 102 and blade 104 may be provided as integral with one another, or alternatively, may be separable.

For the purposes of this disclosure, switches are depicted as switch operators only (e.g., pushbuttons or slider), but may include contacts and other switch components. Additionally, it should be understood that switches may be located other than where depicted herein.

Right and left movement of blade 104 relative to longitudinal axis 106 (FIG. 6), is accomplished by rotating a gear 108 fixed to a cartridge 110 containing an axle 112 on which blade 104 is pivotally mounted to pivot about axis 114. Cartridge 110 is movably contained within handle 102 to accommodate additional adjustments to be described hereinafter.

Motor M1 has a splined output shaft 113 geared to gear 108 fixed to cartridge 110. Operation of motor M1 therefore rotates cartridge 110 and hence blade 104 within handle 102 (FIG. 1) about axis 106.

Figure 3:
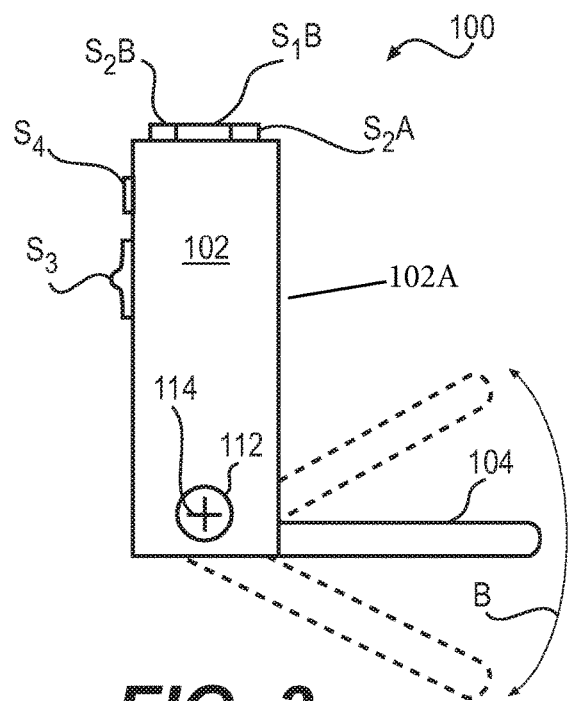
FIG. 3 is a diagrammatic side view of the laryngoscope of FIG. 1, illustrating one powered positional adjustment of the blade, according to at least one aspect of the disclosure.

Referring to FIGS. 1, 3, and 6, blade 104 may be pivotally moved through a vertical path indicated by arrow B to vary an angle between blade 104 and axis 106 of handle 102. This movement is effected by pushbutton switch S2 comprising switches S2A and S2B (FIG. 1). Switches S2A, S2B alternate polarities of DC current applied to motor M2 (FIG. 6) as well as making and breaking circuitry (FIG. 9) serving motor M2. Motor M2 rotates a splined output shaft 116 (seen in end view in FIG. 6) geared to a gear 118.

Figure 4:
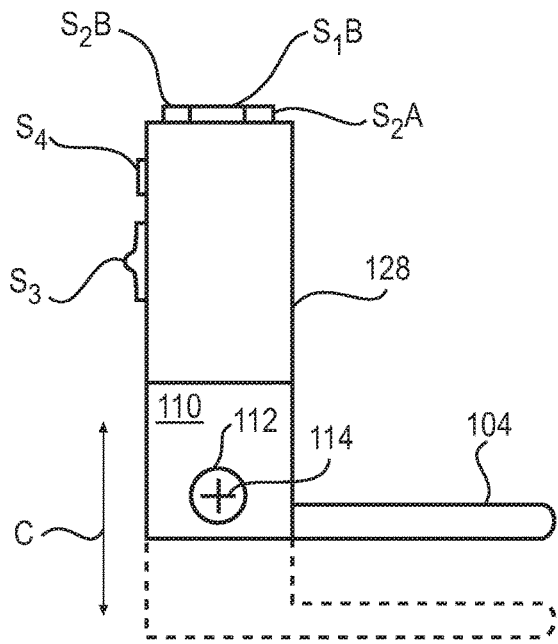
FIG. 4 is a diagrammatic side view of the laryngoscope of FIG. 1, illustrating another powered positional adjustment of the blade, according to at least one aspect of the disclosure.
Figure 7:
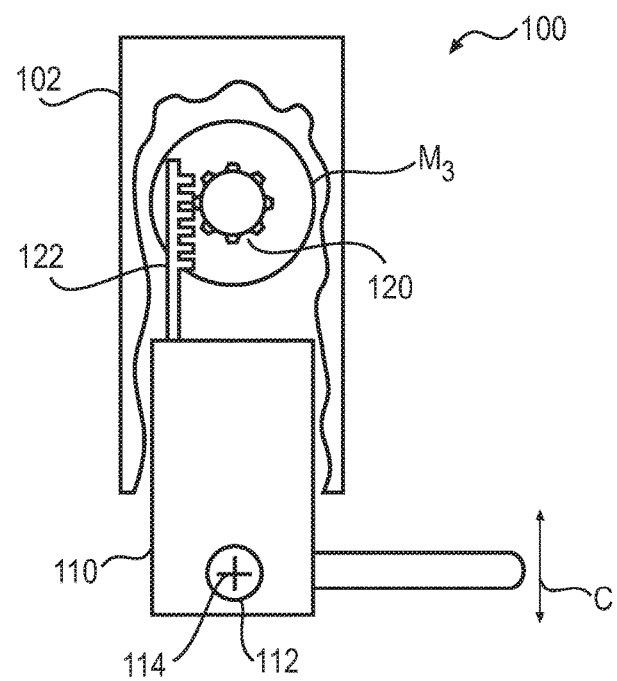
FIG. 7 is a diagrammatic side detail view of internal components of the laryngoscope of FIG. 1, broken away to reveal other internal components, according to at least one aspect of the disclosure.

Referring to FIGS. 1, 4, and 7, blade 104 may be moved along the length of handle 102, as indicated by arrow C. This movement is effected by a sliding switch S3. Sliding switch S3 both alternates polarities of DC current applied to motor M3 (FIG. 7), as well as making and breaking circuitry (FIG. 9) serving motor M3. Referring specifically to FIG. 7, motor M3 has a splined output shaft 120 (seen in end view in FIG. 7) engaging a toothed rack 122 fixed to cartridge 110. Hence operation of motor M3 causes cartridge 110 and blade 104 to translate along handle 102, as indicated by arrow C.

Figure 5:
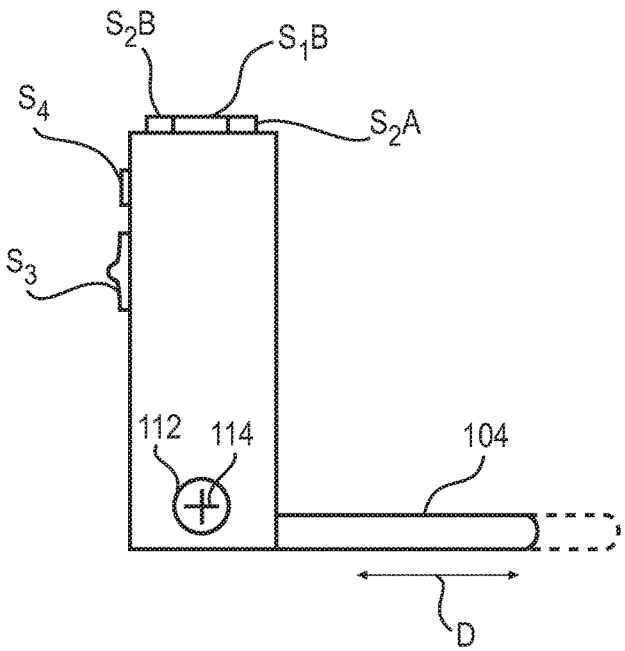
FIG. 5 is a diagrammatic side view of the laryngoscope of FIG. 1, illustrating still a further powered positional adjustment of the blade, according to at least one aspect of the disclosure.
Figure 8:
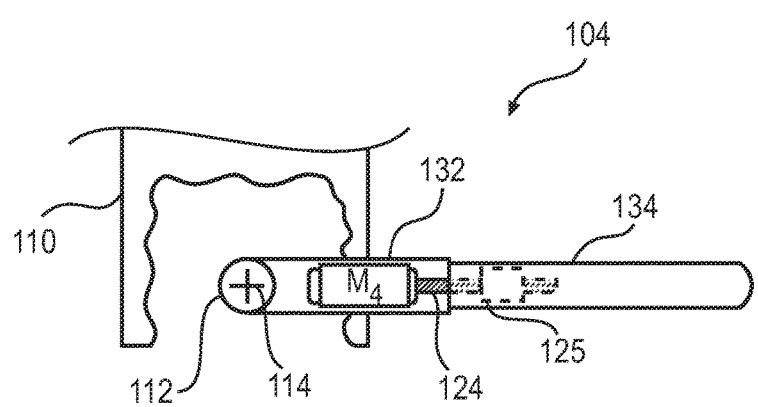
FIG. 8 is a diagrammatic side detail view of internal components of the laryngoscope of FIG. 1, broken away to reveal still other internal components, according to at least one aspect of the disclosure.

Referring to FIGS. 1, 5, and 8, it is also possible to vary exposed length of blade 104 by a switch S4. Switch S4 operates by toggle logic. That is, alternating usages of switch S4 reverse polarity of current applied to motor M4. As seen in FIG. 8, motor M4 has a threaded output shaft 124 engaging a nut 125 held captive and constrained against rotation in telescoping section 132 of blade 104. Rotation of threaded output shaft 124 causes telescoping section 132 to translate along blade 104. Reversible extension 128 of blade 104, indicated by arrow D in FIG. 5, is thereby accomplished by motor M4.

The various motions of blade 104 indicated by arrows A, B, C, and D may be regarded as discrete possible motions of blade 104. One dedicated switch S1, S2, S3, or S4 reversibly controls each one of the discrete possible motions. Therefore, blade 104 has at least two discrete possible motions and a switch (S1, S2, S3 or S4) reversibly controlling each one of the at least two discrete motions.

Laryngoscope 100 further comprises a guide linkage constraining blade 104 to move in at least one predetermined path relative to handle 102. Laryngoscope 100 includes at least one motor M1, M2, M3, or M4 in handle 100, the at least one motor M1, M2, M3, or M4 housed in the handle, having a motion output when the motor M1, M2, M3, or M4 is operating. Laryngoscope 100 includes at least one transmission for each one of the at least one motor M1, M2, M3, or M4, which said at least one transmission moves blade 104 in one of the at least one predetermined path responsive to operation of at least one motor M1, M2, M3, or M4.

The predetermined path may comprise a first predetermined path wherein blade 104 inclines at different angles relative to the length of handle 102 in a plane occupied by a longitudinal center line 106 of handle 102 and a longitudinal center line 138 (FIG. 1) of blade 104. The first predetermined path is illustrated in FIG. 3.

The predetermined path may comprise a second predetermined path wherein blade 104 pivots about axis 106 parallel to the length of handle 102. The second predetermined path lies in a plane perpendicular to longitudinal center line 106 of handle 102, as shown in FIG. 2.

The predetermined path may further comprise a third predetermined path along a plane passing through handle 102, wherein an angle between the plane and blade 104 is constant while blade 104 moves along the plane The third predetermined path is illustrated in FIG. 4.

The predetermined path may further comprise a fourth predetermined path extending transversely relative to the length of handle 102, wherein an angle between the handle and blade 104 remains constant while blade 104 moves transversely relative to handle 102. The fourth predetermined path is illustrated in FIG. 5.

The predetermined path may comprise a first predetermined path wherein blade 104 inclines at different angles relative to the handle 102 of blade 104; a second predetermined path wherein blade 104 pivots about an axis parallel to the length of handle 102; a third predetermined path along the length of handle 102, wherein an angle between handle 102 and blade 104 remains constant while blade 104 moves along a plane extending through handle 102; and a fourth predetermined path extending transversely relative to the length of handle 102, wherein an angle between handle 102 and blade 104 remains constant while blade 104 moves transversely relative to handle 102. If desired, any combination of the predetermined paths described herein may be incorporated into the novel laryngoscope 100.

A transmission is a linkage which transmits motor output to blade 104 and adapts the motor output to effect the appropriate movement of blade 104. In the example of FIG. 6, gear 108 and splined output shaft 116 provide the transmission for accomplishing the movement illustrated in FIG. 2. Also in FIG. 6, axle 112 and splined output shaft 116 provide the transmission for accomplishing the movement illustrated in FIG. 3. In FIG. 7, splined output shaft 120 and toothed rack 122 provide the transmission accomplishing the movement illustrated in FIG. 4. In FIG. 8, threaded output shaft 124 and nut 125, the latter fixed to blade 104, provide the transmission for accomplishing the movement illustrated in FIG. 5.

The structure constraining the blade to move as described is provided by engagement or entrapment of a moved component by a portion of handle 102. For example, an outer housing 128 of handle 102 surrounds cartridge 110, constraining the latter to move in the direction of arrow C when blade 104 moves as illustrated in FIG. 4. Correspondingly, axle 112 is journaled within cartridge 110 such that blade 104 pivots as shown by arrow B in FIGS. 1 and 6. In FIG. 8, projection of a distal telescoping section 134 of blade 104 is guided and constrained by close sliding cooperation with telescoping section 132.

Laryngoscope 100 comprises an electrical power source, electrical circuitry connected to the electrical power source and the at least one motor M1, M2, M3, or M4, and at least one switch S1, S2, S3, or S4 on an exterior of handle 102 for each at least one motor M1, M2, M3, or M4. Each at least one switch S1, S2, S3, S4 is arranged to make and break power from the electrical power source to the at least one motor M1, M2, M3, or M4. The electrical power source comprises battery 130 in handle 102. Alternatively, or in addition to battery 130, where the latter is a rechargeable battery 130, the power source may be a plug and cord assembly 136 (FIG. 1). The plug and cord assembly is connected to the electrical circuitry to enable operation as described herein. Where battery 130 is provided as a rechargeable battery 130, it will be understood to include an AC-to-DC converter and other components required for operability as described herein.

In one implementation of the disclosure, the at least one motor comprises first motor M1 arranged to move blade 104 along the first predetermined path, and the at least one transmission comprises a first transmission arranged to move blade 104 in the first predetermined path responsive to operation of first motor M1, and first switch S1 on handle 102, first switch S1 arranged to make and break power from the electrical circuitry to first motor M1. The at least one motor comprises second motor M2 arranged to move blade 104 along the second predetermined path, and the at least one transmission comprises a second transmission arranged to move blade in the second predetermined path responsive to operation of second motor M2, and second switch S2 on handle 102, second switch S2 arranged to make and break power from the electrical circuitry to second motor M2. The at least one motor comprises third motor M3 arranged to move blade 104 along the third predetermined path, and the at least one transmission comprises a third transmission arranged to move blade 104 in the third predetermined path responsive to operation of third motor M3, and third switch S3 on handle 102, third switch S3 arranged to make and break power from the electrical circuitry to third motor M3. The at least one motor comprises fourth motor M4 arranged to move blade 104 along the fourth predetermined path, and the at least one transmission comprises a fourth transmission arranged to move blade 104 in the fourth predetermined path responsive to operation of fourth motor M4, and fourth switch S4 on handle 102, the fourth switch arranged to make and break power from the electrical circuitry to fourth motor M4.

In an implementation of the disclosure, first switch S1 comprises a first subswitch S1A arranged to operate first motor M1 in a first direction, and a second subswitch S1B arranged to operate first motor M1 in an opposed direction. Second switch S2 comprises a third subswitch 52A arranged to operate second motor M2 in a first direction, and a fourth subswitch 52B arranged to operate second motor M2 in an opposed direction.

In the above implementation, first subswitch S1A, second subswitch S1B, third subswitch S2A, and fourth subswitch S2B are in an array wherein each one of first subswitch S1A, second subswitch S1B, third subswitch S2A, and fourth subswitch S2B is adjacent to two others of first subswitch S1A, second subswitch S1B, third subswitch S2A, and fourth subswitch S2B. First subswitch S1A is opposite second subswitch S1B in the array, and third subswitch S2A is opposite fourth subswitch S2B in the array. This is shown in FIG. 1.

In an implementation of the disclosure, third switch S3 is a slide action switch movable in opposed directions to operate third motor M3 selectively in respective opposed directions. In FIG. 1, the opposed directions are indicated by an arrow E.

Figure 10:
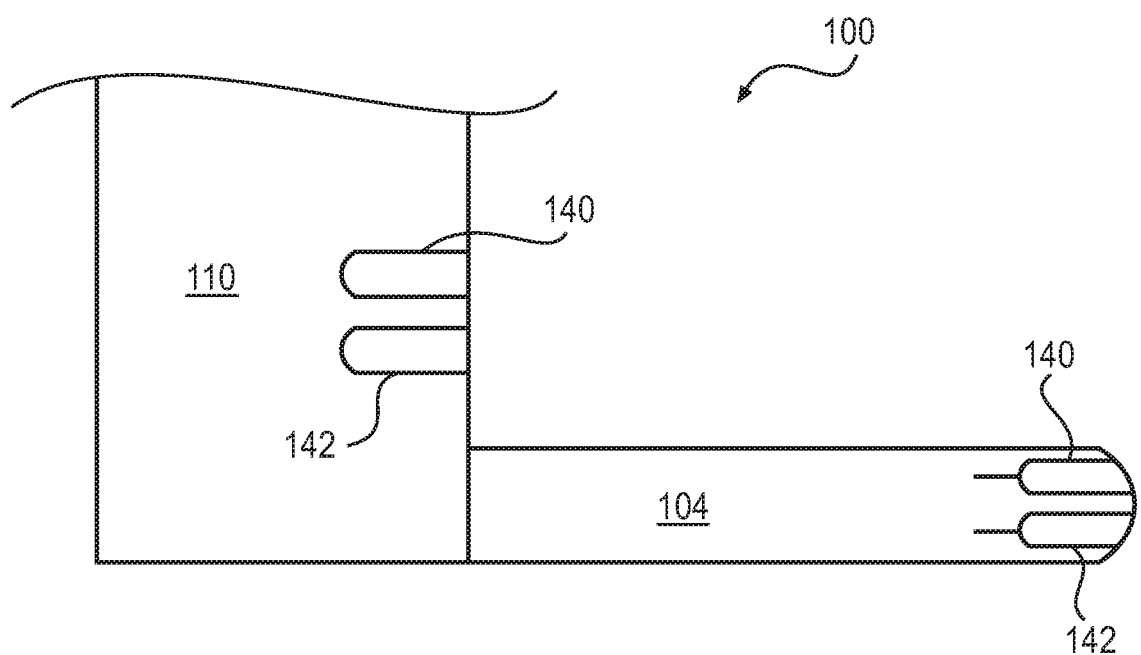
FIG. 10 is a side detail view of optional components of the laryngoscope of FIG. 1, according to at least one aspect of the disclosure.

Optionally, and referring to FIG. 10, laryngoscope 100 comprises a light source 140 operable to project light from laryngoscope 100. In one option, light source 140 is in handle 102. In another option, light source 140 is in blade 104.

In a further option, which may be executed with or without the option for light source 140, laryngoscope 100 further comprises a camera 142 operable to record the environment of blade 104. In laryngoscope 100, camera 142 is in handle 102. Alternatively or in addition to a camera 142 in handle 102, in laryngoscope 100, camera 142 is in blade 104. Power and signals may be conducted in electrical or optic fiber cables (none shown) passing through blade 104 or handle 102, as appropriate.

Mechanical linkages imparting motion to blade 104 from motors M1, M2, M3, and M4 as described above (i.e., splined output shafts 114, 116, 120, and 124, and their associated driven elements), which form a mechanism for moving blade 104 relative to handle 102 may be varied in their nature from the arrangements shown and described herein. For example, linear motors (not shown) rather than rotary output motors may be incorporated into laryngoscope 100.

Location and nature of switches S1, S2, S3 or S4 and their pushbutton operators may be varied from the arrangements shown and described herein.

Figure 9:
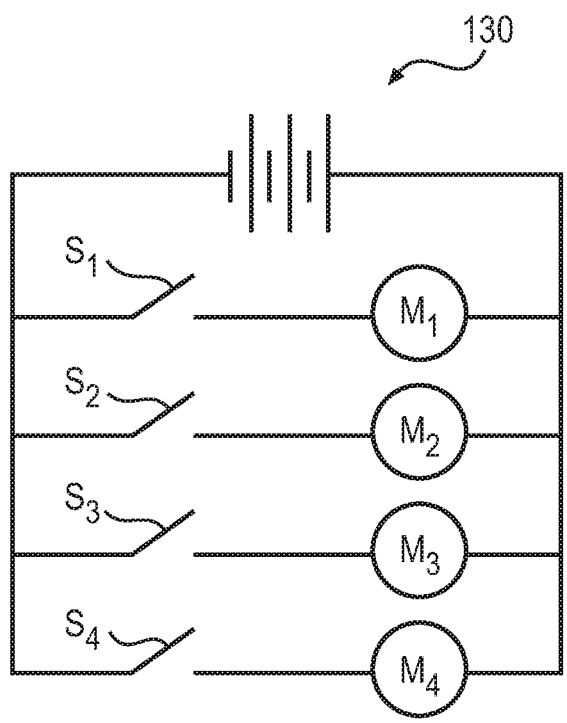
FIG. 9 is an electrical schematic showing a power and control circuit of the laryngoscope of FIG. 1.

FIG. 9 shows power circuitry serving motors M1, M2, M3, and M4. Battery 130 is contained within handle 102. As an alternative, laryngoscope 100 may have a power cord (not shown) for connection to AC power, and an AC-to-DC converter (not shown) in place of battery 130. In a further alternative, laryngoscope 100 may have both an AC power connection with a converter (neither shown), and also a rechargeable battery 130.

As an alternative to electrically powered operation, some positional adjustments of blade 104 may be mechanically accomplished. For example, linkages (not shown) incorporating pusher rods, levers, and rocker arms may be employed where feasible. Functions of laryngoscope 100 described herein in terms of electrical power may in alternative realizations of the disclosure be accomplished mechanically. Piston and cylinder assemblies and other known mechanical arrangements, and pneumatic and/or hydraulic systems may be incorporated, for example.

Although handle 102 has been depicted as a parallelepiped, handle 102 may be rounded, flat and straight, curved, or may reflect oral cavity anatomy. Handle 102 may incorporate a recess or alternatively, an outwardly projecting wall (neither shown) to help direct the endotracheal tube passage towards the larynx.

It is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

It should be understood that the various examples of the apparatus(es) disclosed herein may include any of the components, features, and functionalities of any of the other examples of the apparatus(es) disclosed herein in any feasible combination, and all of such possibilities are intended to be within the spirit and scope of the present disclosure. Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples presented and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims.

What is claimed is:

1. A laryngoscope comprising:
   a handle having a front side, a proximal end, and a distal end;
   a blade movably coupled to the handle and projecting from the front side of the handle proximate the distal end of the handle; and
   a mechanism for moving the blade relative to the handle, the mechanism further comprising:
      a guide linkage constraining the blade to move in at least one predetermined path relative to the handle, wherein the at least one predetermined path is selected from a group consisting of:
      a first predetermined path, wherein the first predetermined path comprises a first designated path traveled on a flat plane by the blade, the flat plane simultaneously bisecting a handle length and a blade length, wherein during the travel an angle between the handle length and the blade length remains constant while the blade translates along the handle length,
      a second predetermined path wherein the second predetermined path comprises a second designated path traveled on a flat plane by the blade, the flat plane simultaneously bisecting a handle length and a blade length, wherein the blade pivots about a fulcrum positioned on the flat plane where the handle and the blade intersect, the pivoting causing a plurality of inclination angles between the blade length and the handle length on the flat plane,
      a third predetermined path wherein the third predetermined path comprises a third designated path traveled on a flat plane by the blade, the flat plane simultaneously bisecting the handle along a substantially widthwise direction thereof and a blade length, wherein during the travel the blade pivots about an axis through the handle length while maintaining a constant angle to the handle, and
      a fourth predetermined path extending transversely relative to a length of the handle, wherein the fourth predetermined path further comprises a fourth designated path traveled on a flat plane by the blade, the flat plane simultaneously bisecting a handle length and a blade length, wherein during the travel an angle between the handle length and the blade length remains constant while the blade moves transversely toward or away from an axis through a center of the blade;
   at least one motor housed in the handle, the at least one motor having a motion output when the motor is operating; and
   at least one transmission for each one of the at least one motors, wherein said at least one transmission moves the blade in the at least one predetermined path responsive to operation of at least one motor.

2. The laryngoscope of claim 1, further comprising:
   at least one motor housed in the handle, the at least one motor having a motion output when the motor is operating;
   at least one transmission for each one of the at least one motors, wherein said at least one transmission moves the blade in the at least one predetermined path responsive to operation of at least one motor;
   an electrical power source;
   electrical circuitry connected to the electrical power source and the at least one motor; and
   at least one switch on an exterior of the handle for each said at least one motor, each said at least one switch arranged to make and break power from the electrical power source to the at least one motor.

3. The laryngoscope of claim 2, wherein the power source comprises a battery in the handle.

4. The laryngoscope of claim 2, wherein the power source comprises a cord and pronged plug assembly.

5. The laryngoscope of claim 2, further comprising a light source operable to project light from the laryngoscope.

6. The laryngoscope of claim 5, wherein the light source is in the handle.

7. The laryngoscope of claim 5, wherein the light source is in the blade.

8. The laryngoscope of claim 2, further comprising a camera operable to record an environment of the blade.

9. The laryngoscope of claim 8, wherein the camera is in the handle.

10. The laryngoscope of claim 8, wherein the camera is in the blade.

11. The laryngoscope of claim 1, wherein the at least one motor comprises:
    a first motor arranged to move the blade along the first predetermined path, and the at least one transmission comprises a first transmission arranged to move the blade in the first predetermined path responsive to operation of the first motor;
    a first switch on the handle, the first switch arranged to make and break power from electrical circuitry to the first motor;
    a second motor arranged to move the blade along the second predetermined path, and the at least one transmission comprises a second transmission arranged to move the blade in the second predetermined path responsive to operation of the second motor, and a second switch on the handle, the second switch arranged to make and break power from the electrical circuitry to the second motor;

a third motor arranged to move the blade along the third predetermined path, and the at least one transmission comprises a third transmission arranged to move the blade in the third predetermined path responsive to operation of the third motor, and a third switch on the handle, the third switch arranged to make and break power from the electrical circuitry to the third motor; and a fourth motor arranged to move the blade along the fourth predetermined path, and the at least one transmission comprises a fourth transmission arranged to move the blade in the fourth predetermined path responsive to operation of the fourth motor, and a fourth switch on the handle, the fourth switch arranged to make and break power from the electrical circuitry to the fourth motor.

12. The laryngoscope of claim 1, further comprising at least one of:
   an electrical assembly comprising:
      an electrical power source;
      electrical circuitry connected to the electrical power source and the at least one motor; and
      at least one switch on an exterior of the handle for each said at least one motor, each said at least one switch arranged to make and break power from the electrical power source to the at least one motor; and
   a mechanical linkage assembly comprising at least one of:
      a mechanical linkage comprising at least one piston and cylinder assembly, creating movement in at least one of the predetermined paths; and
      at least one of a pneumatic system and a hydraulic system, creating movement in at least one of the predetermined paths.

13. A laryngoscope comprising:
   a handle having a front side, a proximal end, and a distal end;
   a blade movably coupled to the handle and projecting from the front side of the handle proximate the distal end of the handle; and
   a mechanism for moving the blade relative to the handle, the mechanism further comprising:
      a guide linkage constraining the blade to move in at least one predetermined path relative to the handle;
      at least one motor housed in the handle, the at least one motor having a motion output when the motor is operating; and
      at least one transmission for each one of the at least one motor, wherein said at least one transmission moves the blade in the at least one predetermined path responsive to operation of a said at least one motor,
   wherein the predetermined path comprises a first predetermined path wherein the blade inclines at different angles relative to a length of the handle in a plane occupied by a longitudinal center line of the handle and a longitudinal center line of the blade, and
   wherein the predetermined path comprises a second predetermined path wherein the blade pivots about an axis parallel to a length of the handle.

14. The laryngoscope of claim 13, further comprising at least one of:
   an electrical assembly comprising:
      an electrical power source;
      electrical circuitry connected to the electrical power source and the at least one motor; and
      at least one switch on an exterior of the handle for each said at least one motor, each said at least one switch arranged to make and break power from the electrical power source to the at least one motor; and
   a mechanical linkage assembly comprising at least one of:
      a mechanical linkage comprising at least one piston and cylinder assembly, creating movement in at least one of said paths; and
      at least one of a pneumatic system and a hydraulic system, creating movement in at least one of said paths.

15. The laryngoscope of claim 14, wherein the power source comprises a battery in the handle.

16. The laryngoscope of claim 14, wherein the power source comprises a cord and pronged plug assembly.

17. The laryngoscope of claim 13, further comprising a light source operable to project light from the laryngoscope.

18. The laryngoscope of claim 17, wherein the light source is in the handle.

19. The laryngoscope of claim 17, wherein the light source is in the blade.

20. The laryngoscope of claim 13, further comprising a camera operable to record an environment of the blade.

21. The laryngoscope of claim 20, wherein the camera is in the handle.

22. The laryngoscope of claim 20, wherein the camera is in the blade.

23. A laryngoscope comprising:
   a handle having a front side, a proximal end, and a distal end;
   a blade movably coupled to the handle and projecting from the front side of the handle proximate the distal end of the handle; and
   a mechanism for moving the blade relative to the handle, the mechanism further comprising:
      a guide linkage constraining the blade to move in at least one predetermined path relative to the handle;
      at least one motor housed in the handle, the at least one motor having a motion output when the motor is operating; and
      at least one transmission for each one of the at least one motor, wherein said at least one transmission moves the blade in the at least one predetermined path responsive to operation of a said at least one motor,
   wherein the predetermined path comprises a first predetermined path wherein the blade inclines at different angles relative to a length of the handle in a plane occupied by a longitudinal center line of the handle and a longitudinal center line of the blade, and
   wherein the predetermined path further comprises a third predetermined path along a plane passing through the handle, wherein an angle between the plane and the blade is constant while the blade moves along the plane.

24. The laryngoscope of claim 23, further comprising at least one of:
   an electrical assembly comprising:
      an electrical power source;
      electrical circuitry connected to the electrical power source and the at least one motor; and
      at least one switch on an exterior of the handle for each said at least one motor, each said at least one switch arranged to make and break power from the electrical power source to the at least one motor; and
   a mechanical linkage assembly comprising at least one of:

a mechanical linkage comprising at least one piston and cylinder assembly, creating movement in at least one of said paths; and at least one of a pneumatic system and a hydraulic system, creating movement in at least one of said paths.

25. The laryngoscope of claim 24, wherein the power source comprises a battery in the handle.

26. The laryngoscope of claim 24, wherein the power source comprises a cord and pronged plug assembly.

27. The laryngoscope of claim 23, further comprising a light source operable to project light from the laryngoscope.

28. The laryngoscope of claim 27, wherein the light source is in the handle.

29. The laryngoscope of claim 27, wherein the light source is in the blade.

30. The laryngoscope of claim 23, further comprising a camera operable to record an environment of the blade.

31. The laryngoscope of claim 30, wherein the camera is in the handle.

32. The laryngoscope of claim 30, wherein the camera is in the blade.

33. A laryngoscope comprising:
a handle having a front side, a proximal end, and a distal end;
a blade movably coupled to the handle and projecting from the front side of the handle proximate the distal end of the handle; and
a mechanism for moving the blade relative to the handle, the mechanism further comprising:
a guide linkage constraining the blade to move in at least one predetermined path relative to the handle;
at least one motor housed in the handle, the at least one motor having a motion output when the motor is operating; and
at least one transmission for each one of the at least one motor, wherein said at least one transmission moves the blade in the at least one predetermined path responsive to operation of a said at least one motor,
wherein the predetermined path comprises a first predetermined path wherein the blade inclines at different angles relative to a length of the handle in a plane occupied by a longitudinal center line of the handle and a longitudinal center line of the blade, and
wherein the predetermined path further comprises a fourth predetermined path extending transversely relative to a length of the handle, wherein an angle between the handle and the blade remains constant while the blade moves transversely relative to the handle.

34. The laryngoscope of claim 33, further comprising at least one of:
an electrical assembly comprising:
an electrical power source;
electrical circuitry connected to the electrical power source and the at least one motor; and
at least one switch on an exterior of the handle for each said at least one motor, each said at least one switch arranged to make and break power from the electrical power source to the at least one motor; and
a mechanical linkage assembly comprising at least one of:
a mechanical linkage comprising at least one piston and cylinder assembly, creating movement in at least one of said paths; and
at least one of a pneumatic system and a hydraulic system, creating movement in at least one of said paths.

35. The laryngoscope of claim 34, wherein the power source comprises a battery in the handle.

36. The laryngoscope of claim 34, wherein the power source comprises a cord and pronged plug assembly.

37. The laryngoscope of claim 33, further comprising a light source operable to project light from the laryngoscope.

38. The laryngoscope of claim 37, wherein the light source is in the handle.

39. The laryngoscope of claim 37, wherein the light source is in the blade.

40. The laryngoscope of claim 33, further comprising a camera operable to record an environment of the blade.

41. The laryngoscope of claim 40, wherein the camera is in the handle.

42. The laryngoscope of claim 40, wherein the camera is in the blade.

43. A laryngoscope comprising:
a handle having a front side, a proximal end, and a distal end;
a blade movably coupled to the handle and projecting from the front side of the handle proximate the distal end of the handle; and
a mechanism for moving the blade relative to the handle, the mechanism further comprising:
a guide linkage constraining the blade to move in at least one predetermined path relative to the handle;
at least one motor housed in the handle, the at least one motor having a motion output when the motor is operating; and
at least one transmission for each one of the at least one motor, wherein said at least one transmission moves the blade in the at least one predetermined path responsive to operation of a said at least one motor,
wherein the at least one predetermined path comprises:
a first predetermined path wherein the blade inclines at different angles relative to the handle;
a second predetermined path wherein the blade pivots about an axis parallel to a length of the handle;
a third predetermined path along the length of the handle, wherein an angle between the handle and the blade remains constant while the blade moves along a plane extending through the handle; and
a fourth predetermined path extending transversely relative to the length of the handle, wherein an angle between the handle and the blade remains constant while the blade moves transversely relative to the handle.

44. The laryngoscope of claim 43, wherein the at least one motor comprises:
a first motor arranged to move the blade along the first predetermined path, and the at least one transmission comprises a first transmission arranged to move the blade in the first predetermined path responsive to operation of the first motor;
a first switch on the handle, the first switch arranged to make and break power from he electrical circuitry to the first motor;
a second motor arranged to move the blade along the second predetermined path, and the at least one transmission comprises a second transmission arranged to move the blade in the second predetermined path responsive to operation of the second motor, and a second switch on the handle, the second switch arranged to make and break power from the electrical circuitry to the second motor;
a third motor arranged to move the blade along the third predetermined path, and the at least one transmission comprises a third transmission arranged to move the blade in the third predetermined path responsive to operation of the third motor, and a third switch on the handle, the third switch arranged to make and break power from the electrical circuitry to the third motor; and a fourth motor arranged to move the blade along the fourth predetermined path, and the at least one transmission comprises a fourth transmission arranged to move the blade in the fourth predetermined path responsive to operation of the fourth motor, and a fourth switch on the handle, the fourth switch arranged to make and break power from the electrical circuitry to the fourth motor.

45. The laryngoscope of claim 44, wherein
the first switch comprises a first subswitch arranged to operate the first motor in a first direction, and a second subswitch arranged to operate the first motor in an opposed direction; and
wherein the second switch comprises a third subswitch arranged to operate the second motor in a first direction, and a fourth subswitch arranged to operate the second motor in an opposed direction.

46. The laryngoscope of claim 45, wherein the first subswitch, the second subswitch, the third subswitch, and the fourth subswitch are in an array wherein each one of the first subswitch, the second subswitch, the third subswitch, and the fourth subswitch is adjacent to two others of the first subswitch, the second subswitch, the third subswitch, and the fourth subswitch, wherein the first subswitch is opposite the second subswitch in the array, and the third subswitch is opposite the fourth subswitch in the array.

47. The laryngoscope of claim 45, wherein the third switch is a slide action switch movable in opposed directions to operate the third motor selectively in respective opposed directions.

48. The laryngoscope of claim 43, further comprising at least one of:
an electrical assembly comprising:
an electrical power source;
electrical circuitry connected to the electrical power source and the at least one motor; and
at least one switch on an exterior of the handle for each said at least one motor, each said at least one switch arranged to make and break power from the electrical power source to the at least one motor; and
a mechanical linkage assembly comprising at least one of:
a mechanical linkage comprising at least one piston and cylinder assembly, creating movement in at least one of said paths; and
at least one of a pneumatic system and a hydraulic system, creating movement in at least one of said paths.

49. The laryngoscope of claim 48, wherein the power source comprises a battery in the handle.

50. The laryngoscope of claim 48, wherein the power source comprises a cord and pronged plug assembly.

51. The laryngoscope of claim 43, further comprising a light source operable to project light from the laryngoscope.

52. The laryngoscope of claim 51, wherein the light source is in the handle.

53. The laryngoscope of claim 51, wherein the light source is in the blade.

54. The laryngoscope of claim 43, further comprising a camera operable to record an environment of the blade.

55. The laryngoscope of claim 54, wherein the camera is in the handle.

56. The laryngoscope of claim 54, wherein the camera is in the blade.

57. A laryngoscope comprising:
a handle having a front side, a proximal end, and a distal end;
a blade movably coupled to the handle and projecting from the front side of the handle proximate the distal end of the handle; and
a mechanism for moving the blade relative to the handle, the mechanism further comprising:
a guide linkage constraining the blade to move in a designated path traveled on a flat plane by the blade, the flat plane simultaneously bisecting a handle length and a blade length, wherein during the travel an angle between the handle length and the blade length remains constant while the blade translates along the handle length;
at least one motor housed in the handle, the at least one motor having a motion output when the motor is operating; and
at least one transmission for each one of the at least one motors, wherein said at least one transmission moves the blade in the at least one predetermined path responsive to operation of at least one motor.

58. A laryngoscope comprising:
a handle having a front side, a proximal end, and a distal end;
a blade movably coupled to the handle and projecting from the front side of the handle proximate the distal end of the handle; and
a mechanism for moving the blade relative to the handle, the mechanism further comprising:
a guide linkage constraining the blade to move in a designated path traveled on a flat plane by the blade, the flat plane simultaneously bisecting a handle length and a blade length, wherein the blade pivots about a fulcrum positioned on the flat plane where the handle and the blade intersect, the pivoting causing a plurality of inclination angles between the blade length and the handle length on the flat plane;
at least one motor housed in the handle, the at least one motor having a motion output when the motor is operating; and
at least one transmission for each one of the at least one motors, wherein said at least one transmission moves the blade in the at least one predetermined path responsive to operation of at least one motor.

59. A laryngoscope comprising:
a handle having a front side, a proximal end, and a distal end;
a blade movably coupled to the handle and projecting from the front side of the handle proximate the distal end of the handle; and
a mechanism for moving the blade relative to the handle, the mechanism further comprising:
a guide linkage constraining the blade to move in a designated path traveled on a flat plane by the blade, the flat plane simultaneously bisecting the handle along a substantially widthwise direction thereof and a blade length, wherein during the travel the blade pivots about an axis through the handle length while maintaining a constant angle to the handle;
at least one motor housed in the handle, the at least one motor having a motion output when the motor is operating; and
at least one transmission for each one of the at least one motors, wherein said at least one transmission moves the blade in the at least one predetermined path responsive to operation of at least one motor.

60. A laryngoscope comprising:

a handle having a front side, a proximal end, and a distal end;

a blade movably coupled to the handle and projecting from the front side of the handle proximate the distal end of the handle; and a mechanism for moving the blade relative to the handle, the mechanism further comprising:

a guide linkage constraining the blade to move in a designated path traveled on a flat plane by the blade, the flat plane simultaneously bisecting a handle length and a blade length, wherein during the travel an angle between the handle length and the blade length remains constant while the blade moves transversely toward or away from an axis through a center of the blade;

at least one motor housed in the handle, the at least one motor having a motion output when the motor is operating; and at least one transmission for each one of the at least one motors, wherein said at least one transmission moves the blade in the at least one predetermined path responsive to operation of at least one motor.

* * * * *